(12) United States Patent
Lin et al.

(10) Patent No.: US 6,564,624 B2
(45) Date of Patent: May 20, 2003

(54) FUEL DRIVEABILITY INDEX SENSOR AND METHOD

(75) Inventors: Yingjie Lin, El Paso, TX (US); Han-Sheng Lee, Bloomfield Hills, MI (US); Su-Chee Simon Wang, Troy, MI (US); David Kay Lambert, Sterling Heights, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/924,873

(22) Filed: Aug. 8, 2001

(65) Prior Publication Data

US 2003/0029234 A1 Feb. 13, 2003

(51) Int. Cl.$^7$ .............................................. G01M 15/00
(52) U.S. Cl. ...................................................... 73/118.1
(58) Field of Search ............................ 73/61.45, 61.49, 73/61.79, 64.53, 579, 596, 597, 599, 602, 118.1; 250/339.09, 339.12, 343; 204/415, 421, 424, 430, 431, 432

(56) References Cited

U.S. PATENT DOCUMENTS 5,522,980 A  *  6/1996  Hobbs et al. ................ 204/432
5,750,995 A  *  5/1998  Clarke ..................... 250/339.12
6,032,516 A  *  3/2000  Takahashi et al. .......... 73/64.53
6,250,137 B1  *  6/2001  Takahashi et al. .......... 73/64.53

* cited by examiner

Primary Examiner—Max Noori
Assistant Examiner—Monica D. Harrison
(74) Attorney, Agent, or Firm—Margaret A. Dobrowitsky

(57) ABSTRACT

A sensor and method for measuring the volatility of liquid gasoline by estimating its driveability index includes a sensing element having an interdigitated array of electrically conducting capacitor plates arranged to retain a predetermined volume of gasoline, the volatility of which is to be measured. The sensing element is mounted in a vehicle to be in contact with the flow of gasoline while the engine is running so that a volume certain of gasoline is drawn between and remains within the electrically conducting plates when the engine is turned off. The sensing element is connected to circuitry used to measure the change in capacitance of the sensing element as a function of time while simultaneously measuring the temperature change of the sensing element as the volume of gasoline retained by the sensing element is evaporated over time. The measurements obtained by the circuitry are used in estimating the drivability index of the gasoline.

4 Claims, 2 Drawing Sheets

FUEL DRIVEABILITY INDEX SENSOR AND METHOD

TECHNICAL FIELD

This invention relates to an on-board sensor and method for using the same to measure the volatility of a sample of gasoline by measuring the change in capacitance of a sensing element as a function of time and temperature and using those measurements to estimate the driveability index of the sample.

BACKGROUND OF THE INVENTION

It is known in the art relating to automotive engines, that the key gasoline characteristic for good driveability is volatility. Volatility is especially important at the time an engine is started because liquid gasoline must evaporate and mix with air to form a combustible mixture. If too little gasoline is added, the engine will not start; if gasoline beyond that needed to initiate combustion is added, then extra hydrocarbons from an unburned portion of gasoline are found in the exhaust. Moreover, because gasoline sold in the United States varies in volatility, there is a tradeoff in engine design between low hydrocarbon emissions and good driveability with low volatility fuel.

To describe the effect of gasoline volatility on the cold start and warmup driveability of a vehicle, a driveability index (DI) has been developed. For gasoline that does not contain oxygenates such as ethanol or methyl tertiary-butyl ether (MTBE), the definition of DI is based on a laboratory test (ASTM D 86) in which a sample of gasoline is distilled as its temperature is raised. The fraction distilled is measured as a function of temperature and $$DI = 1.5T_{10} + 3T_{50} + T_{90}$$

where $T_x$ is the temperature in degrees Fahrenheit at which x% of the gasoline sample has been distilled.

Experiments have shown that even if DI is held constant, the presence of oxygenates in a fuel changes the cold start and warm-Lip driveability of a vehicle. With oxygenated gasoline, an expression that provides better correlation to engine performance is the New Driveability Index (NDI):

$$NDI = DI + 43.2\delta_{MTBE} + 86.2\delta_{EtOH}$$

where the variables $\delta_{MTBE}$ and $\delta_{EtOH}$ are 1 if about 15% methyl tertiary-butyl ether or 10% ethanol, respectively, is present, and zero otherwise.

Although both DI and NDI are defined in terms of a laboratory procedure, they can also be estimated. One known way to estimate DI is by measuring the fuel's infrared transmission spectrum. While this approach has proven useful in refineries where the feedstocks are known, it has not been accepted as an accurate way to characterize the DI of finished gasoline in the field.

It is particularly desirable to estimate DI/NDI on-board a vehicle. To provide customer satisfaction, engines are calibrated to reliably start with fuel of the lowest expected. This is done by increasing the amount of fuel in the air/fuel mixture. Consequently, for most starts, the engine's air/fuel ratio is richer than optimum. Some of this extra gasoline passes unburned into the exhaust. This is particularly detrimental at the time of a cold start because the catalytic converter is too cold to be active. The added hydrocarbon concentration is typically emitted to the environment.

Estimating DI or NDI on-board would permit the air/fuel ratio to be more precisely controlled. The engine would be calibrated to reliably start while extra fuel would only be added when needed to compensate for fuel volatility. On the average, less fuel would be used for cold starts resulting in a decrease in fleet-average exhaust hydrocarbon emissions. This decrease in air pollution is an important environmental benefit.

SUMMARY OF THE INVENTION

The present invention provides an on-board sensor and method of using the same to determine or estimate DI (or NDI) by measuring changes in electrical capacitance of a fuel-filled sensing element as the sensing element is heated to evaporate the fuel within it.

While the engine is running, gasoline flows over a two-piece sensing element having a plurality of interdigitated plates that are arranged to retain a volume certain of gasoline between them after the engine is turned off. Because the retained volume is controlled by the spacing between the interdigitated plates, the present invention eliminates the need to supply a precisely predetermined volume of sample to the sensing element for testing. In the preferred embodiment, a small amount of fuel (e.g. in the range of 0.04–0.1 ml) remains in the sensing element every time the engine is turned off.

The sensing element is then heated by means of a ceramic heater. The sensor's change in capacitance and temperature over time is measured with circuitry operatively connected to the sensing element. Because the sensing element exhibits a relatively large change in capacitance (in the range of 4 pF) simple, relatively inexpensive circuitry may be implemented.

When the sensor reaches a predetermined level of capacitance, the heater is turned off and the measured data, which is representative of the volume and temperature of the sample, is sent to the microcontroller of the vehicle, which calculates DI, or NDI, as the case may be. The DI or NDI so calculated correlates well with laboratory calculated DI and NDI. Moreover, the measured change in capacitance over time between the full and empty states indicates whether or not the tested fuel contained ethanol. The calculated value of DI or NDI is then stored for the next cold start when it may be used for setting the desired air/fuel ratio at the time of starting.

These and other features and advantages of the invention will be more fully understood from the following description of certain specific embodiments of the invention taken together with the accompanying drawings.

DESCRIPTION OF THE PREFERRED EMBODIMENT

Figure 1:
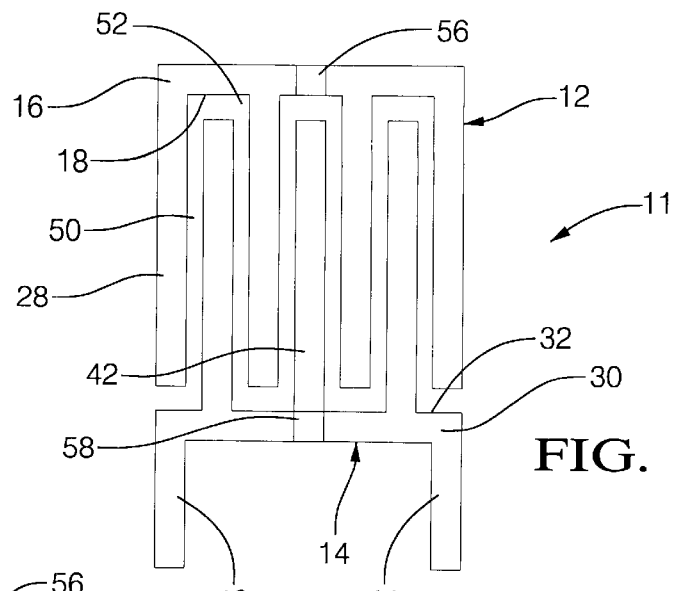
FIG. 1 is a top view of the sensing element of the present invention.

Referring now to the drawings in detail, numeral 10 generally indicates a sensor according to the present invention. As shown in FIGS. 1–4, the sensor 10 includes a sensing element 11 comprised of a pair of interdigitated members 12 and 14.

Member 12 has a base plate 16 having a surface 18 bounded by ends 20, 22, 24, 26. Each one of a plurality of parallel capacitor plates 28 is mounted to the base surface 18 perpendicularly, equally spaced one from one another from end 20 to end 22 to form slots extending from end 24 to end 26.

An opposing member 14 includes a base plate 30 having a surface 32 bounded by ends 34, 36, 38, 40. Each one of a plurality of parallel capacitor plates 42 is mounted to the base surface 32 perpendicularly, equally spaced one from one another between locations spaced from each end 34 and 36 to form slots extending from end 38 to end 40.

The base plate 30 of member 14 further includes a pair of wings 44, 46 mounted on and perpendicular to surface 48 at end 34 and 36. The wings 44 and 46 are used to grasp member 14.

Figure 4:
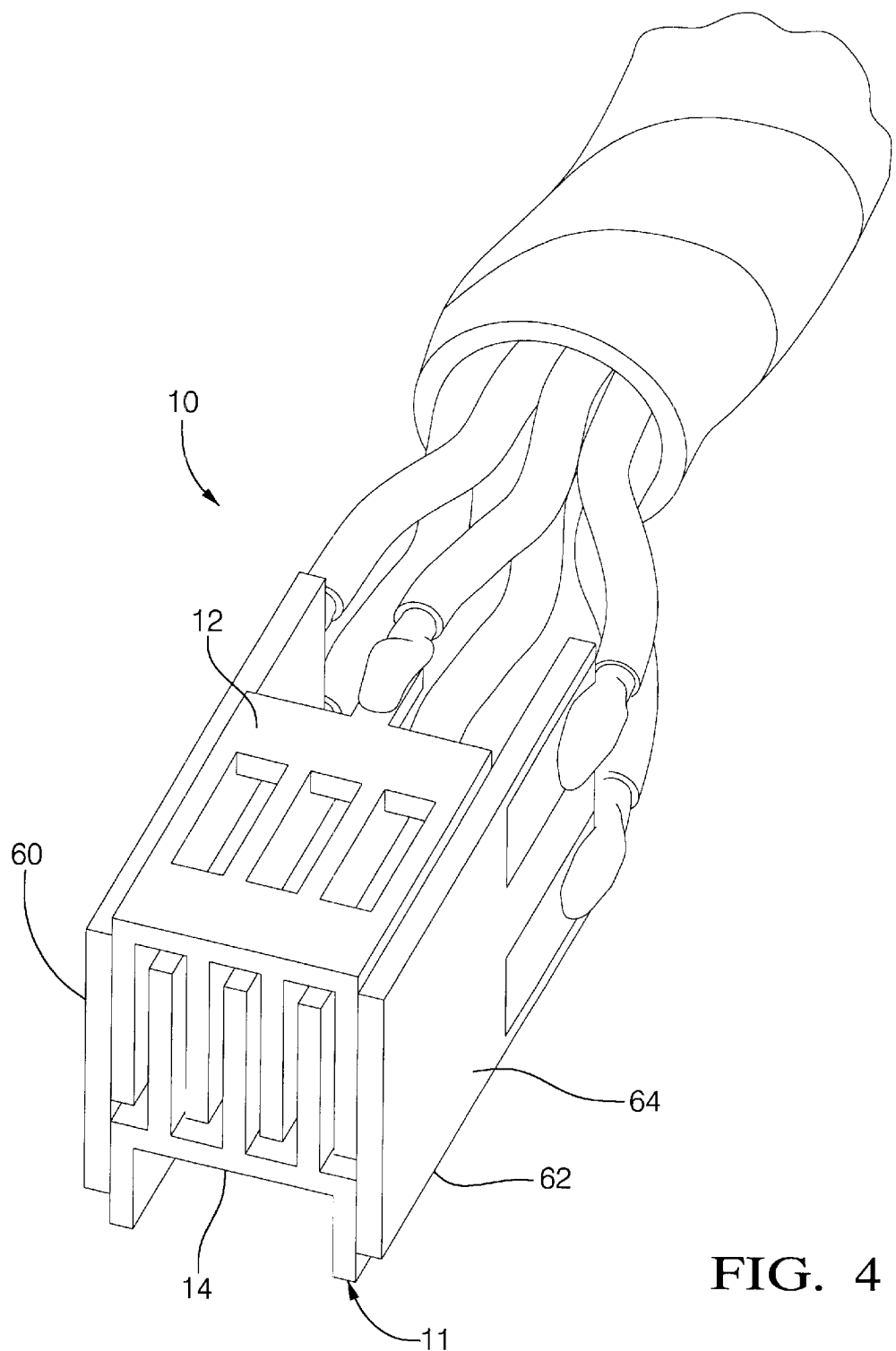
FIG. 4 is a perspective view of the sensor of the present invention.

As shown in FIGS. 1 and 4, the plates 42 of member 14 are interdigitated with the plates 28 of member 12, leaving a gap 50 in the range of 0.2–0.8 mm between each alternating plate, and a gap 52 in the range of 0.2–0.8 mm between the free end of each one of the plates 28, 42 and its respective opposing base surface 18 or 32.

In operation, the sensing element 11 is mounted within the fuel tank of a vehicle so that it is in contact with a flow of gasoline when the engine is running but is above the maximum fuel level in the tank. When the vehicle engine is stopped, and the fuel drains away from the sensor, a known volume of gasoline is drawn between the plates 28, 42 by capillary attraction, completely filling the gaps 50, 52.

Figure 5:
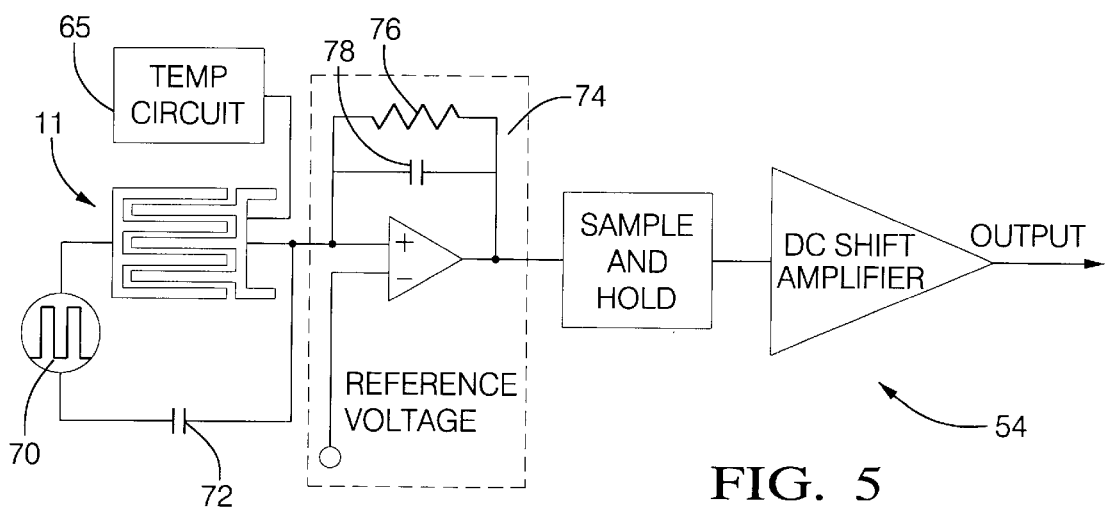
FIG. 5 is a schematic diagram of a signal processing circuit of the present invention.

The sensing element 11 is connected with a capacitance measuring circuit 54 of FIG. 5 at terminals 56 and 58 which are integral with base plates 16 and 30 at ends 24 and 38 respectively.

As shown in FIG. 4, the sensing element 11 is mounted between a pair of ceramic plates 60 and 62 to which a heating element 64 is connected. A temperature measuring circuit 65 is also attached to the sensing element 11 to monitor the change in temperature of the sensing element 11 over time.

Figure 2:
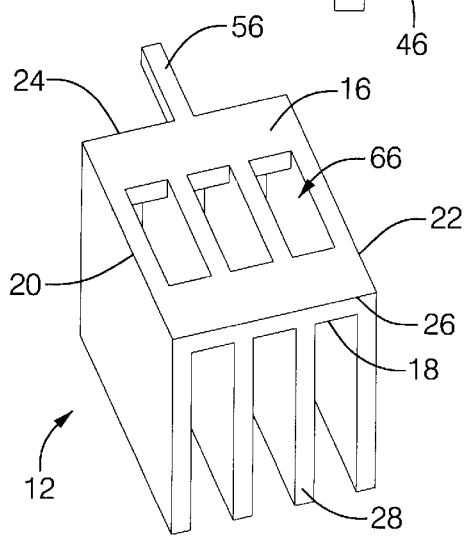
FIG. 2 is a perspective view of a first member of the sensing element of the present invention.
Figure 3:
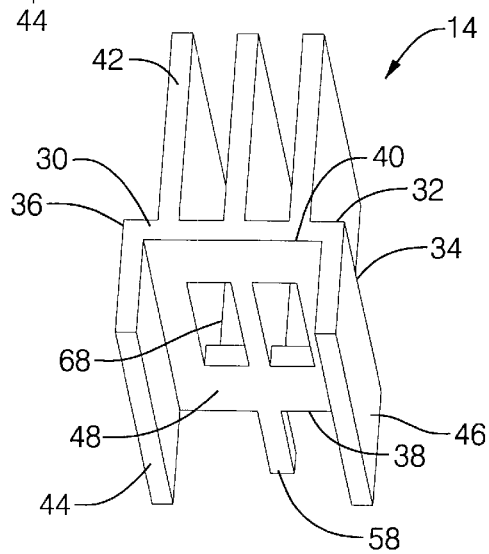
FIG. 3 is a perspective view of an opposing member to that of FIG. 2.

As the sensing element 11 is heated, the fuel filling the gaps 50, 52 begins to evaporate. As shown in FIG. 2, base plate 16 further includes a plurality of openings 66 disposed between the parallel plates 28. Base plate 30 includes similar openings 68 disposed between its parallel plates 42. Openings 66, 68 facilitate vapor release from the sensing element 11 during heating.

Sensing element 11 is connected at its terminals 56 and 58 to circuit 54 which provides an excitation signal in the form of a square wave having relatively high frequency (in the range of 50 kHz–100 kHz). A signal generator 70 and sensing element 11 are connected in series with a balancing capacitor 72 which, in the preferred embodiment, has a fixed capacitance close to the capacitance of the empty sensing element 11, to generate an input current to a current-to-voltage converter 74.

The current-to-voltage converter 74 includes a resistor 76 having a relatively large resistance (in the mega ohm range) which functions to discharge the capacitance of the sensing element 11. Resistor 76 is in parallel with a feedback capacitor 78 having a relatively small capacitance (in the 20 pF range).

Current-to-voltage converter 74 produces an output voltage that is directly proportional to the input current, which is in turn directly proportional to the impedance difference between the sensing element 11 and the balancing capacitor 72. Because the capacitance of the balancing capacitor 72 is fixed, changes in the impedance difference are equal to the change in capacitance of the sensing element 11.

The output of the current-to-voltage converter 74 is changed into a DC signal as shown in FIG. 5 to obtain an output voltage that is directly proportional to the sample volume.

Output from circuit 54 and the temperature measurement circuit is provided to a microcontroller (not shown) that is programmed to perform DI or NDI calculations depending on the capacitance versus temperature relationships.

While the invention has been described by reference to certain preferred embodiments, it should be understood that numerous changes could be made within the spirit and scope of the inventive concepts described. Accordingly, it is intended that the invention not be limited to the disclosed embodiments, but that it have the full scope permitted by the language of the following claims.

What is claimed is:

1. A sensor for use in measuring the volatility of liquid gasoline by estimating its driveability index, said sensor comprising:
    a sensing element having an interdigitated array of electrically conducting capacitor plates arranged to retain a predetermined volume of gasoline, the volatility of which is to be measured; and
    circuitry operatively connected with said sensing element to measure a change in capacitance of said sensing element as a function of time while simultaneously measuring a temperature change of the sensing element as the volume of gasoline retained by the sensing element is evaporated over time for use in estimating the driveability index of the gasoline.

2. The sensor of claim 1, wherein said circuitry includes a temperature measuring circuit and a circuit for measuring the capacitance change of said sensing element as said sensing element is heated over time.

3. The sensor of claim 2, wherein said circuit for measuring the capacitance of said sensing element includes a current-to-voltage converter.

4. A method of providing an output usable for measuring the volatility of liquid gasoline, comprising the steps of:
    providing a sensor including a sensing element having an interdigitated array of electrically conducting capacitor plates arranged to retain a predetermined volume of gasoline;
    connecting said sensing element to electrical circuitry adapted to measure a change in capacitance of said sensing element over time while simultaneously measuring a change in temperature of the sensing element;
    placing said sensing element in contact with a flow of gasoline while the engine is running so that a volume certain of gasoline is drawn between said electrically conducting plates;
    removing the flow of gasoline from the sensing element when the engine is turned off;
    heating the sensing element to cause part of the retained volume of gasoline to evaporate; and
    measuring the change in capacitance of the sensing element as a function of the temperature of the sensing element over time to provide an output usable in calculating the driveability index of the gasoline.

* * * * *